United States Patent
Thomas et al.

(10) Patent No.: US 7,597,744 B2
(45) Date of Patent: Oct. 6, 2009

(54) USE OF MOLECULAR SIEVES FOR THE REMOVAL OF HFC-23 FROM FLUOROCARBON PRODUCTS

(75) Inventors: Raymond H. Thomas, Pendleton, NY (US); Rajiv R. Singh, Getzville, NY (US); Thomas W. Morris, Mendham, NJ (US); Roy P. Robinson, Cheektowaga, NY (US)

(73) Assignee: Honeywell International Inc., Morristown, NJ (US)

( * ) Notice: Subject to any disclaimer, the term of this patent is extended or adjusted under 35 U.S.C. 154(b) by 403 days.

(21) Appl. No.: 11/485,519

(22) Filed: Jul. 12, 2006

(65) Prior Publication Data

US 2008/0011159 A1  Jan. 17, 2008

(51) Int. Cl.
*B01D 53/02*  (2006.01)
(52) U.S. Cl. .............................. 95/142; 95/141; 95/143; 95/900; 95/903; 423/240 S
(58) Field of Classification Search .................. 95/900, 95/903, 141–143; 423/240 S
See application file for complete search history.

(56) References Cited

U.S. PATENT DOCUMENTS

| | | | |
|---|---|---|---|
| 3,899,310 A | 8/1975 | Chi et al. | |
| 7,341,984 B2 * | 3/2008 | Wilson et al. | 510/408 |
| 2003/0034309 A1 | 2/2003 | Ohno et al. | |
| 2006/0019857 A1 * | 1/2006 | Wilson et al. | 510/408 |
| 2006/0140836 A1 | 6/2006 | Oka | |

FOREIGN PATENT DOCUMENTS

| | | |
|---|---|---|
| EP | 1442779 | 8/2004 |
| JP | 08081399 | 3/1996 |
| WO | WO 96/30109 | 10/1996 |
| WO | WO 01/83412 | 11/2001 |

OTHER PUBLICATIONS

Translation of JP08-081399, Ono Hiromoto et al., Mar. 26, 1996.*

* cited by examiner

*Primary Examiner*—Duane Smith
*Assistant Examiner*—Christopher P Jones
(74) *Attorney, Agent, or Firm*—Colleen D. Szuch

(57) ABSTRACT

Use of molecular sieves to reduce the amount of trifluoromethane (HFC-23) present in a mixture of HFC-23 with other materials, particularly from mixtures containing HFC-23 and trifluoroiodomethane ($CF_3I$).

9 Claims, No Drawings

USE OF MOLECULAR SIEVES FOR THE REMOVAL OF HFC-23 FROM FLUOROCARBON PRODUCTS

FIELD OF THE INVENTION

This invention relates to the use of molecular sieves to separate trifluoromethane (HFC-23) from a mixture of HFC-23 with other gases, particularly from mixtures containing HFC-23 and trifluoroiodomethane ($CF_3I$).

BACKGROUND TO THE INVENTION

Concern over human impact on climate change prompted a 1997 United Nations conference in Kyoto, Japan. The resulting Kyoto Protocol seeks to stabilize greenhouse gases in the atmosphere "at a level that would prevent dangerous anthropogenic interference with the climate system."

Perfluorocarbon compounds (PFC's), hydrofluorocarbon compounds (HFC's), chlorofluorocarbons (CFC's), hydrochlorofluorocarbon compounds (HCFC's), and their like, have been widely used in a broad variety of industrial, commercial, consumer and public use applications and uses. Recently, concern has increased about potential damage to the earth's atmosphere and climate, and certain perfluorocarbon compounds (PFC's), hydrofluorocarbon compounds (HFC's), chlorofluorocarbons (CFC's), hydrochlorofluorocarbon compounds (HCFC's), and their like, have been identified as particularly problematic in this regard, at least in part because of the greenhouse gas effect and relatively high global warming potentials (GWP) associated with those compounds. In view of the relatively high GWP of these compounds there has been a vigorous search for alternative compounds of lower GWP to replace these compounds of higher GWP in those use, application and compositions to be used in such applications and uses.

The entry into force of the Kyoto Protocol on Feb. 16, 2005 has accelerated the need for elimination or greatly reducing the use of GWP compositions. Thus, there is a continual search for new fluorocarbon and hydrofluorocarbon fluids for use, especially in air conditioning and refrigeration uses, so as to reduce global warming and for lessening possible depletion of the ozone layer.

One of the key ingredients in the search for such new low global warming potential (GWP) candidates is trifluoroiodomethane ($CF_3I$). In such the compositions there is often or usually present a lubricant. Any of a variety of conventional lubricants may be used. An important requirement for the lubricant is that, when in use in a refrigerant system, there must be sufficient lubricant returning to the compressor of the system such that the compressor is lubricated. Thus, suitability of a lubricant for any given system is determined partly by the refrigerant/lubricant characteristics and partly by the characteristics of the system in which it is intended to be used. Examples of suitable lubricants include mineral oil, alkyl benzenes, polyol esters, including polyalkylene glycols, PAG oil, and the like. However, it has been discovered that these lubricants, which are hydrogen bearing for the most part, by interaction with trifluoroiodomethane results in the production of highly undesirable trifluoromethane (HFC-23) which has a high GWP. This HFC-23 breakdown product is very undesirable in a product or composition that is intended to have and should have a low GWP. Thus, there is a need to be able to remove HFC-23 from such products or compositions, whether the HFC-23 is present as a breakdown product or as an undesirable component initially present in the product or composition. While there have been a number of processes proposed for the separation of HFC-23 from product or compositions with other lesser GWP compounds, most of these methods are expensive and inefficient. Thus, there is a need for an effective, efficient and simple way to remove HFC-23 from such products or compositions.

SUMMARY OF THE INVENTION

In accordance with this invention it has been discovered that the use of molecular sieves of an acceptable effective pore size provides a process for trapping or separating HFC-23 from its mixture with materials, such as fluids or gases, particularly iodocarbons, whose molecular diameters are greater than that of HFC-23 so as to reduce the amount of HFC-23 in the mixture. The process may be conducted with any suitable molecular sieve and is suitable for separating HFC-23 from its mixture with any other material that has a molecular diameter, polarity or shape such that a separation is possible. Given the complexity of the separation process, it is very difficult to predict which molecular sieves will separate various combinations of materials. The process of this invention is particularly suitable for removing HFC-23 from refrigerant compositions, especially refrigerant compositions containing iodocarbons, such as trifluoroiodomethane. The process of the invention is particularly suitable for removing HFC-23 produced in-situ by interaction between the components of a refrigerant composition containing an iodocarbon, such as trifluoroiodomethane, and a lubricant.

DETAILED DESCRIPTION OF THE INVENTION

In accordance with this invention there is provided a process for trapping or separating at least a portion of HFC-23 from its mixture with other materials, such as fluids or gases, particularly iodocarbons so as to reduce the amount of HFC-23 in the mixture. While it is difficult to predict molecular sieve separations, the inventors have shown that iodocarbons, particularly trifluoroiodomethane are such that they can be separated from fluorocarbons such as R-23 by the use of molecular sieves whose diameters are about 5 angstroms. The process may be conducted with any suitable molecular sieve and is suitable for separating HFC-23 from its mixture with any other fluid or gas that has a molecular diameter greater than the molecular diameter of HFC-23. The process of this invention is particularly suitable for removing HFC-23 from refrigerant compositions, especially refrigerant compositions containing iodocarbons, such as trifluoroiodomethane. The process of the invention is particularly suitable for removing HFC-23 produced in-situ by interaction between the components of a refrigerant composition containing an iodocarbon, such as trifluoroiodomethane, and optionally a lubricant. For the purpose of this invention an "iodocarbon" is any compound containing iodine and carbon atoms and optionally other atoms.

The product containing the HFC-23 as an impurity in a composition with other desirable materials, such as fluid(s) or gas(es), can be brought into contact with the molecular sieve in either the liquid or gas phase, in a process that may be either a continuous or a batch process to adsorb the HFC-23 and thereby separate and remove it from the other desirable fluid (s) or gas(es). The level to which the HFC-23 is reduced is dependent upon the capacity of the molecular sieve and the equilibrium between the HFC-23 and the mixture of gases and in the molecular sieve itself. It is preferred to use as much molecular sieve as necessary to reduce the level of HFC-23 impurity to less than about 500 ppm, preferably to level of less than about 100 ppm, and more preferably to a level of less than about 10 ppm The process of this invention may employ any suitable molecular sieve including, but not limited to, suitable zeolite and carbon molecular sieves. The suitable molecular sieve must have an acceptable effective pore size such as to adsorb HFC-23 but not adsorb the other favorable and desired fluids or gases. It has been discovered that 4A molecular sieves (having an effective pore size of 4 Å) will not separate HFC-23 from trifluroiodomethane, however 5A series molecular sieves (with an effective pore size of 5 Å) will very effectively achieve such separation of HFC-23 from trifluroiodomethane. Thus, it is believed that HFC-23 has an effective molecular diameter of less than 5 Å and that the effective molecular diameter of trifluoroiodomethane is greater than 5 Å. Thus, given the difference in effective molecular diameters separation of HFC-23 from trifluoroiodomethane can be effected by using molecular sieves whose diameters are less than the effective molecular diameter of trifluoroiodomethane.

In a similar manner, HFC-23 can be adsorbed and separated from a composition containing HFC-23 and another fluid or gas having a greater molecular diameter than the HFC-23. For example, if the other fluid or gas is one having an effective molecular diameter of 10 Å, molecular sieves having an effective pore size of from 5 Å to 9 Å may be employed to effect the adsorption and separation of HFC-23 from the composition. Thus, for any particular separation of HFC-23 from other fluid(s) or gas(es), molecular sieves of an "effective pore size" are those molecular sieves that operate to preferentially reduce the amount of, or remove at least some of, HFC-23. Such molecular sieves having an effective pore size are generally those having an effective pore size of from 5 Å to a pore size less than the effective molecular diameter of the other fluid(s) or gas(es).

Molecular sieves useful in the process of this invention are available from a variety of sources, including but not limited to, zeolite molecular sieves from Universal oil Products, Grace and Aldrich Chemical Co., and carbon molecular sieves from Aldrich Chemical Co., Chemos GmbH of Germany and Dayung Chemical Co., Ltd. of China.

The invention is illustrated by, but limited too, the following examples.

AW500 zeolite molecular sieve (Aldrich chemical Co.) having an effective pore size of 5 Å was placed in an oven at 300° F. (149° C.) for four hours to activate the molecular sieve. This activated molecular sieve was employed in the following Examples 1, 2 and 4. The molecular sieves employed in Example 3 and Comparative Examples 1 and 2 were activated in a similar manner.

EXAMPLE 1

2.26 Grams of activated AW500 molecular sieve were placed into a stainless steel cylinder. 2.04 Grams of the refrigerant mixture trifluoroiodomethane/HFO-1234 (tetrafluoropropene) (25/75) were added to the cylinder. The refrigerant mixture contained 11 wt. % HFC-23. After one hour the gas in the cylinder was examined and found to contain only 3.2 wt % HFC-23 because of the adsorption of the HFC-23 by the molecular sieve.

EXAMPLE 2

2.26 Grams of activated AW500 molecular sieve were placed into a stainless steel cylinder. 2.04 Grams of the refrigerant mixture trifluoroiodomethane/HFO-1234yf (1,1,1,2-tetrafluoropropene) (25/75) were added to the cylinder. The refrigerant mixture contained 4.1 wt. % HFC-23. After one hour the gas in the cylinder was examined and found to contain only 0.15 wt % HFC-23 because of the adsorption of the HFC-23 by the molecular sieve.

EXAMPLE 3

465 Grams of 5A molecular sieve were placed into a stainless steel column. 1344 Grams of the refrigerant mixture of trifluoroiodomethane containing 0.235 wt HFC-23 was passed through the column containing the molecular sieve. The effluent gas was examined by chromatography and HFC-23 was not detectable.

EXAMPLE 4

2.5 Grams of activated AW500 molecular sieve were placed into a stainless steel cylinder. 2.5 Grams of the refrigerant mixture trifluoroiodomethane/HFO-1234 (tetrafluoropropene) (25/75) were added to the cylinder. The refrigerant mixture contained 0.5 wt. % HFC-23. After one hour the gas in the cylinder was examined and found to contain only 0.003 wt % HFC-23 because of the adsorption of the HFC-23 by the molecular sieve.

COMPARATIVE EXAMPLE 1

2.5 Grams of activated 4A molecular sieve (having an effective pore size of 4 Å) were placed into a stainless steel cylinder. 2.5 Grams of the refrigerant mixture trifluoroiodomethane/HFO-1234 (tetrafluoropropene) (25/75) were added to the cylinder. The refrigerant mixture contained 0.5 wt. % HFC-23. After one hour the gas in the cylinder was examined and found to contain only 0.42 wt % HFC-23 showing that the amount of HFC-23 remained essentially unchanged after exposure to the 4A molecular sieve.

COMPARATIVE EXAMPLE 2

2.5 Grams of activated XH7 molecular sieve (having an effective pore size of 4 Å) were placed into a stainless steel cylinder. 2.5 Grams of the refrigerant mixture trifluoroiodomethane/HFO-1234 (tetrafluoropropene) (25/75) were added to the cylinder. The refrigerant mixture contained 0.5 wt. % HFC-23. After one hour the gas in the cylinder was examined and found to contain only 0.45 wt % HFC-23 showing that the amount of HFC-23 remained essentially unchanged after exposure to the 4A molecular sieve Having described the invention in detail by reference to the preferred embodiments and specific examples thereof, it will be apparent that modifications and variations are possible without departing from the spirit and scope of the disclosure and claims.

We claim:

1. A process for separating trifluoromethane from its mixture with an iodocarbon used as a refrigerant, wherein the process comprises:
   producing said mixture comprising said iodocarbon and said trifluoromethane, and
   contacting said mixture with a molecular sieve whose effective pore size is of a size to adsorb or separate at least a portion of said trifluoromethane from said iodocarbon.

2. A process according to claim 1 wherein the iodocarbon is trifluoroiodomethane and the molecular sieve has a pore size whose diameter is smaller than the effective molecular diameter of the trifluoroiodomethane.

3. The process according to claim 2 wherein the molecular sieve is a zeolite.

4. The process according to claim 2 wherein the molecular sieve is a carbon molecular sieve.

5. A process according to claim 2 wherein the molecular sieve has effective pore size of about 5 Angstroms in diameter.

6. A process according to claim 3 wherein the molecular sieve has effective pore size of about 5 Angstroms in diameter.

7. A process according to claim 1 wherein the amount of trifluoromethane separated from the refrigerant mixture is an amount that results in the mixture containing about 10 ppm or less of trifluoromethane after the separation.

8. The process according to claim 1 wherein said molecular sieve has an effective pore size in the range between about 5 Angstroms to less than the effective molecular diameter of the other non-trifluoromethane fluid(s) or gas(es) in said refrigerant mixture.

9. The process according to claim 1, wherein said refrigerant mixture is contacted with said molecular sieve in either a liquid or gas phase.

* * * * *